United States Patent [19]

Michelotti et al.

[11] Patent Number: 5,254,584
[45] Date of Patent: Oct. 19, 1993

[54] N-ACETONYLBENZAMIDES AND THEIR USE AS FUNGICIDES

[75] Inventors: Enrique L. Michelotti, Fort Washington; Robert R. Raney, Newtown Square; David H. Young, Ambler, all of Pa.

[73] Assignee: Rohm and Haas Company, Philadelphia, Pa.

[21] Appl. No.: 993,158

[22] Filed: Dec. 18, 1992

[51] Int. Cl.$^5$ ............... A01N 47/48; A01N 37/18; A61K 31/165; C07C 235/12
[52] U.S. Cl. ................... 514/514; 514/519; 514/617; 514/619; 514/640; 558/14; 558/17; 558/49; 558/392; 564/161; 564/166; 564/253; 564/254
[58] Field of Search ............... 564/161, 166, 253, 254; 514/617, 619, 640, 514, 519; 558/14, 17, 49, 392

[56] References Cited

U.S. PATENT DOCUMENTS 3,661,991 5/1972 McNulty et al. .
3,751,239 8/1973 McNulty et al. .................. 71/118
4,822,902 4/1989 Carley et al. ..................... 558/14

Primary Examiner—Allen J. Robinson
Assistant Examiner—B. Bembenick
Attorney, Agent, or Firm—Kevin E. McVeigh

[57] ABSTRACT

Certain N-acetonylbenzamides exhibit low phytotoxicity and are useful for control of a wide range of fungi, including phytopathogenic fungi of the classes Oomycetes, Ascomycetes, Deuteromycetes and Basidiomycetes.

30 Claims, No Drawings

N-ACETONYLBENZAMIDES AND THEIR USE AS FUNGICIDES

TECHNICAL FIELD

This invention relates to fungicidal compounds and to a method of controlling phytopathogenic fungi and, more particularly, to certain N-acetonylbenzamides that exhibit high fungicidal activity and low phytotoxicity.

BACKGROUND

It is known that benzamides of the class N-(1,1-dialkyl-3-chloroacetonyl) substituted benzamides exhibit fungicidal activity, see, e.g. U.S. Pat. Nos. 3,661,991 and 3,751,239. However, such compounds also exhibit phytotoxic activity to a degree which severely limits their practical use. U.S. Pat. No. 4,822,902 discloses N-acetonylbenzamides wherein the substituents on the carbon of the acetonyl group may be other than a hydrogen atom or a chlorine atom, which exhibit reduced phytotoxicity and which are of greater practical value in controlling phytopathogenic Oomycetes and some fungi of the classes Deuteromycetes, Ascomycetes, and Basidiomycetes on crops such as, e.g. tomatoes and grapes. While the compounds disclosed in the '902 patent exhibit a sufficiently favorable balance of fungicidal activity and phytotoxicity to be of practical use in controlling phytopathogenic fungi, there is a constant interest in compounds which provide an even more favorable balance of high fungicidal activity and low phytotoxicity.

DETAILED DESCRIPTION OF THE INVENTION

Phytopathogenic fungi are controlled by applying a fungicidally effective amount of a compound of the structural formula (1):

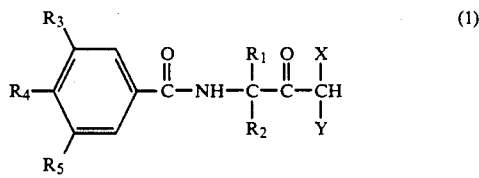

wherein:

$R_1$ and $R_2$ are each independently H, $(C_1-C_4)$alkyl, $(C_2-C_6)$alkenyl or $(C_2-C_6)$alkynyl;

$R_3$, $R_4$ and $R_5$ are each independently H, halo, $(C_1-C_4)$alkyl, $(C_2-C_6)$alkenyl, $(C_2-C_6)$alkynyl or $CR_6=NOR_7$, provided that at least one of $R_3$, $R_4$ and $R_5$ is $CR_6=NOR_7$;

$R_6$ is H, $(C_1-C_4)$alkyl, $(C_2-C_6)$alkenyl or $(C_2-C_6)$alkynyl;

$R_7$ is H, $(C_1-C_4)$alkyl, $(C_2-C_6)$alkenyl, $(C_2-C_6)$alkynyl or $(C_1-C_4)$alkylcarbonyloxy$(C_1-C_4)$alkyl; and X and Y are each independently H, halo, cyano, thiocyanato, isothiocyanato or $(C_1-C_4)$alkylsulfonyloxy; or by applying fungicidally effective amounts of an agronomically acceptable salt of the compound of formula 1.

Halo means chloro, fluoro, bromo, or iodo.

$(C_1-C_4)$alkyl means a straight or branched alkyl group having one to four carbon atoms and includes methyl, ethyl, n-propyl, isopropyl, n-butyl, iso-butyl, sec-butyl and t-butyl.

$(C_2-C_6)$alkenyl means a straight or branched alkenyl group having from two to six carbon atoms and include, e.g. ethenyl, 2-propenyl, 2-butenyl, 1-methylethenyl, 2-methyl-2-propenyl.

$(C_2-C_6)$alkynyl means straight or branched alkynyl group having two to six carbon atoms and includes, e.g. ethynyl, 2-propynyl, 2-butynyl.

$(C_1-C_4)$alkylcarbonyloxy$(C_1-C_4)$alkyl includes, e.g., methylcarbonyloxymethyl, methylcarbonyloxyethyl, methylcarbonyloxpropyl, methylcarbonyloxybutyl, ethylcarbonyloxymethyl, ethylcarbonyloxyethyl, ethylcarbonyloxypropyl, ethylcarbonyloxybutyl, propylcarbonyloxyethyl, propylcarbonyloxypropyl, butylcarbonyloxyethyl and butylcarbonyloxybutyl.

$(C_1-C_4)$alkylsulfonyloxy includes, e.g., methylsulfonyloxy, ethylsulfonyloxy, propylsulfonyloxy and butylsulfonyloxy.

Thiocyanato means —SCN.

Isothiocyanato means —NCS.

Agronomically acceptable salts include, e.g. metal salts such as sodium, potassium, calcium and magnesium, ammonium salts such as isopropylammonium and trialkylsulfonium salts such as trimethylsulfonium.

In a preferred embodiment, $R_1$ and $R_2$ are each $(C_1-C_4)$alkyl, $R_3$ is $CR_6=NOR_7$, $R_4$ is H, $(C_1-C_4)$alkyl or halo, $R_5$ is H, $(C_1-C_4)$alkyl, halo or $CR_6=NOR_7$, $R_6$ is H or $(C_1-C_4)$alkyl, $R_7$ is H, $(C_1-C_4)$alkyl or $(C_1-C_4)$alkylcarbonyloxy$(C_1-C_4)$alkyl, X is chloro or thiocyanato and Y is chloro or, more preferably, H.

In a highly preferred embodiment, $R_1$ is ethyl, $R_2$ is methyl, $R_3$ is $CR_6=NOR_7$, $R_4$ and $R_5$ are each independently H, methyl or chloro, $R_6$ is methyl or, more preferably, H, $R_7$ is H, ethyl or, more preferably, methyl, X is chloro and Y is chloro or, more preferably, H. More preferably, $R_4$ is H and $R_5$ is chloro or methyl.

In an alternative preferred embodiment, $R_1$ is ethyl, $R_2$ is methyl, $R_4$ is $CR_6=NOR_7$, $R_3$ and $R_5$ are each independently H, methyl or chloro, $R_6$ is H or methyl, $R_7$ is H, methyl or ethyl, X is chloro and Y is H.

In another alternative preferred embodiment, $R_1$ is ethyl, $R_2$ is methyl, $R_3$ and $R_5$ are each $CR_6=NOR_7$, $R_4$ is H, $R_6$ is H or methyl, $R_7$ is H, methyl or ethyl, X is chloro and Y is H.

The compounds of the present invention are useful in controlling a broad spectrum of phytopathogenic fungi, e.g. fungi of the classes Oomycetes, Deuteromycetes and Ascomycetes, on such crops as grapes, tomatoes, cucumbers and apples and exhibit high fungicidal activity and low phytotoxicity in such applications.

The compounds of the present invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled. The fungicidally effective amount of compound of the present invention is typically from about 0.01 kg compound/hectare to about 20 kg compound/hectare, preferably from about 0.1 kg compound/hectare to about 5 kg compound/hectare and more preferably from about 0.125 kg compound/hectare to about 0.5 kg compound/hectare.

The compounds of the present invention are useful for the control of phytopathogenic fungi on crops and may be used as seed protectants, soil fungicides and/or foliar fungicides. As a seed protectant, a compound of the present invention is counted on seed at a dosage rate of about 10 grams (gm) compound/50 kilograms (kg) seed to about 20 gm compound/50 kg seed. As a soil fungicide, a compound of the present invention can be incorporated in the soil or applied to the surface of the soil at a dosage rate of about 0.5 kg compound/hectare to about 20 kg compound/hectare, preferably at a rate of about 1 kg compound/hectare to about 5 kg compound/hectare. As a foliar fungicide, a compound of the present invention is applied to growing plants at a dosage rate of about 0.1 kg compound/hectare to about 5 kg compound/hectare and preferably at a rate of about 0.125 kg compound/hectare to about 0.5 kg compound/hectare.

For the above-disclosed purposes, these compounds can be used in the technical or pure form as prepared, as solutions or as formulations. The compounds are usually taken up in an agronomically acceptable carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers* and *Detergents*, *McCutcheon's Emulsifiers* and *Detergents/Functional Materials* and *McCutcheon's Functional Materials* all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentration of active compound in the solution can vary from 1% to 90%, with a preferred range being 5% to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%.

Dusts are prepared by mixing the compounds of the present invention salts and complexes thereof with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration. The compounds of the present invention can also be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), ethyl 1-(butylcarbamoyl)-2-benzimidazole carbamate (benomyl), 2-4′-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinolozolin); 3-(3,5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-dichlorophenoxy)-alpha-(1,1-dimethylethyl)-1H-1,2,4-triazole-1-ethanol (triadimenol); 1-(4-chlorophenoxy)-3,3-dimethyl-1-(1H-1,2,4-triazol-1-yl)-2-butanone (triadimefon); beta-[1,1′-biphenyl]-4-yloxyl]-alpha-(1,1-dimethylethyl)-1H-1,2,4-triazole-1-ethanol (bitertanol); 2,3-dichloro-N-(4-fluorophenyl)maleimide (fluoroimide); 1-[2-(2,4-dichlorophenyl)-4-propyl-1,3-dioxolan-2-ylmethyl]-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha(-phenyl)-alpha-(2,4-dichlorophenyl)-5-pyrimidinylmethanol (triarimol), cis-N-[1,1,2,2-tetrachloroethyl)thio]-4-cyclohexene-1,2-dicarboximide, 3-[2-(3,5-dimethyl-2-oxycyclohexyl)-2-hydroxy]glutarimide (cycloheximide), dehydroacetic acid, N-(1,1,2,2-tetrachloroethylthio)-3a,4,7,7a-tetrahydrophthalimide (captafol), butyl-2-ethylamino-4-hydroxy-6-methylpyrimidine (ethirimol), acetate of 4-cyclodecyl-2,6-dimethyl-morpholine (dodemorph), 4-[3-(4-chlorophenyl)-3-(3,4-dimethoxyphenyl)acryloyl]morpholine (dimethomorph) and 6-methyl-2-oxo-1,3-dithiolo[4,5-b]-quinoxaline (quinomethionate).

(d) miscellaneous halogenated fungicides such as: tetrachloro-p-benzoquinone (chloranil), 2-3-dichoro-1,4-napththoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sulfone, dodecylguanidine acetate (dodine), aluminum tris-o-ethyl phosphonate (fosetyl-al), N-(2,6-dimethylphenyl)-N-(methoxyacetyl)alanine methyl ester (metalaxyl) and other alkaline fungicides, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3,-methoxycarbony-2-thioureido) benzene (thiophanate-methyl), and 2-cyano-N-(ethylamino)carbonyl)-2-(methoxyimine)acetamide (cymoxanil).

The benzamides of the present invention can be prepared using conventional synthesis techniques, e.g., that shown in Scheme A set forth below (wherein $R_{10}$ is chloro or methyl, $R_{11}$ is H or methyl, $R_{12}$ is H or alkyl and Z is H or methyl).

For example, compounds of formula I can be prepared by treating acetylenic amides (II) with halogen or halogen source at a temperature of $-78°$ C. in the presence of a solvent such as methylene chloride, to given an intermediate oxazoline (III) which is readily hydrolyzed under acidic conditions using hydrochloric acid and methanol or tetrahydrofuran as solvent at a temperature of 40° C. to 50° C. The starting acetylenic amides can be prepared by reaction of the corresponding aromatic acyl chloride (IV) and an acetylenic amine (V) in the presence of a base such as triethylamine using methylene chloride, tetrahydrofuran or ethyl ether combined with dimethylformamide as solvents as room temperature, followed by addition of the corresponding alkoxyl amine hydrochloride in the presence of dimethylformamide and triethylamine.

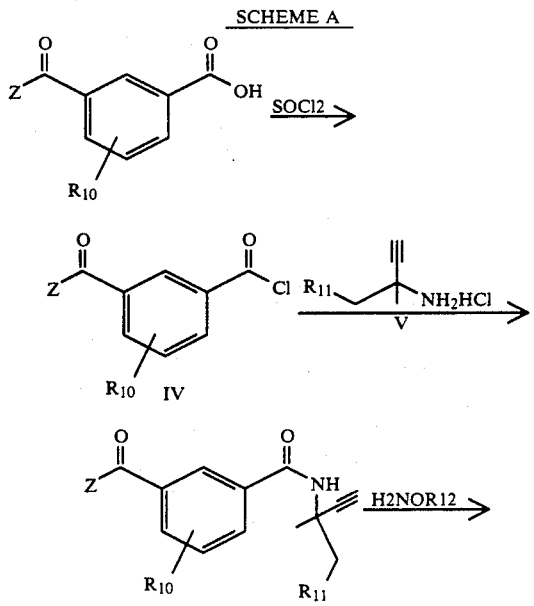

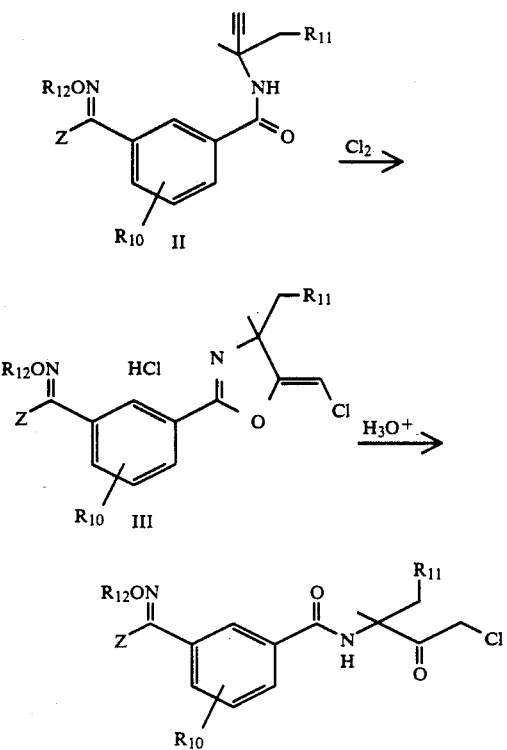

The aromatic acyl chloride (IV) can be prepared, e.g., from the corresponding methyl-substituted benzoic acid as shown in Scheme B set forth below (wherein $R_{13}$ is 4-chloro; 3-chloro; or 3-methyl).

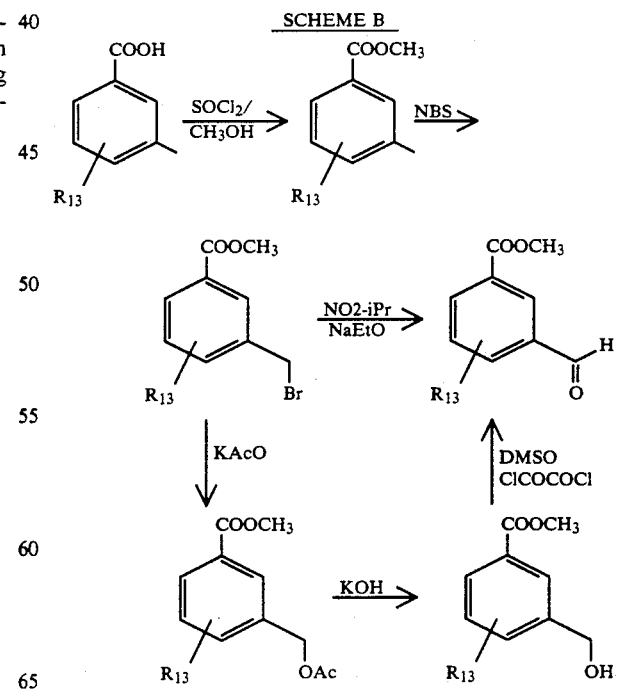

The substituted 3-hydroxymethyl benzoic acid intermediate derivatives can also be prepared, e.g., by Scheme C set forth below (wherein $R_{14}$ is 4-chloro, 3-chloro or 3-methyl).

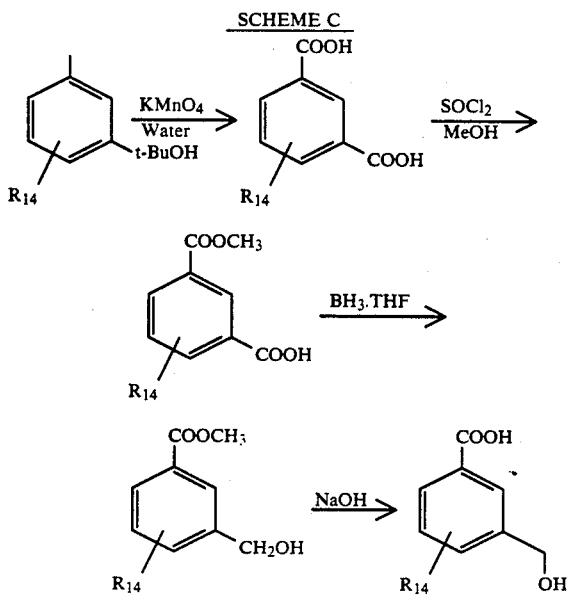

The acetylenic amine (V) can be prepared, e.g., from the corresponding commercially available acetylenic alcohol (VI), as indicated in Scheme D set forth below:

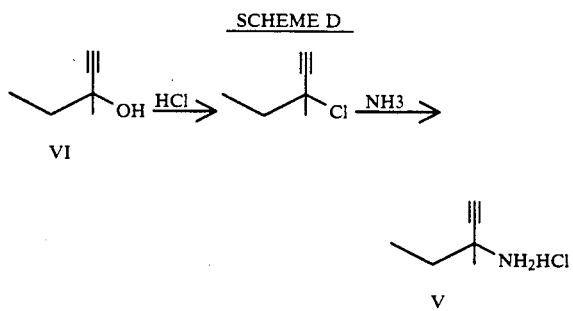

Exemplary compounds of the present invention were prepared as set forth below in Examples 1 to 20.

EXAMPLE 1

3-(3'-Methoxyiminomethylbenzamido)-1-chloro-3-methylpentan-2-one a) Preparation of 3-Formylbenzoyl chloride A mixture of 3-formylbenzoic acid (84 grams (g), 0.558 moles), thionyl chloride (80.5 g, 0.71 moles), and dimethylformamide (3 milliliters (ml)), in toluene (500 ml) was slowly warmed to 70° C. and stirred at that temperature for 2 hours. The toluene was eliminated in the rotavap to yield 97.7 g of 3-formylbenzoyl used in the next step as such.

b) Preparation of N-(3-Methylpent-1-yne)-3-methoxyiminomethylbenzamide

To a cooled, well stirred mixture of 3-methyl-1-pentyn-3-amine hydrochloride (76.6 g, 0.57 moles), and dimethylformamide (500 ml) was added dropwise triethylamine (117 g, 1.147 mole) over 30 minutes. When the addition was completed, the resulting mixture was stirred another 30 minutes at 0° C. To the resulting mixture was added dropwise a solution of 3-formylbenzoyl chloride (96.5 g, approx. 0.57 mole) dissolved in tetrahydrofurane (100 ml), keeping the temperature between 5° to 10° C. When the addition was completed, the resulting mixture was stirred another 1 hour at room temperature. To the well stirred mixture was added (dropwise) a solution of methoxylamine hydrochloride (47.8 g, 0.57 mole) in dimethylformamide (275 ml) at room temperature, followed by the dropwise addition of triethylamine (58.3 g, 0.57 mole) all the while keeping the temperature below 20° C. The resulting mixture was stirred overnight at room temperature. The reaction mixture was poured into ice-water (1 liter) and extracted with ethyl acetate (3×400 ml). The combined organic layers were washed with water (2×300 ml), then with 5% aqueous sodium bicarbonate (2×300 ml), and then with brine (1×400 ml), and dried over anhydrous sodium sulfate. The solvent was then eliminated in a rotavap yielding 121.3 g of N-(3-methylpent-1-yne)-3-methoxyiminomethylbenzamide as an oil used as such in the next step.

c) Preparation of of 2-(3'-methoxyiminomethylphenyl)-4-ethyl-4-methyl-5-chloromethylene oxazoline hydrochloride In a 1 liter, three-necked, round-bottomed flask fitted with a mechanical stirrer, a thermometer and a 250 ml addition funnel were dissolved 29.0 g, 0.1121 moles of N-(3-methylpent-1-yne)-3-methoxyiminomethylbenzamide in a mixture of 110 ml of methylene chloride and 110 ml of hexane. The resulting mixture was cooled down to −50° C. and a cold chlorine solution (8 g of chlorine in 152 g of a 1:1 mixture by volume of methylene chloride and hexane) was added very slowly. When the addition was completed, the reaction mixture was stirred at −65° C. for 30 minutes and warmed slowly to room temperature and then washed with water (2×75 ml). The solvent was then evaporated from the mixture in a rotavap yielding 31.8 g of the expected 2-(3'-methoxyiminomethylphenyl)-4-ethyl-4-methyl-5-chloromethylene oxazoline hydrochloride as a light yellow oil which was used as such in the next step.

d) Preparation of N-[3'-(1'-chloro-3'-methyl-2'-oxopentan)]-3-methoxyiminomethyl-5-chloro-benzamide 73.0 g (0.22 moles) of 2-(3'methoxyiminomethylphenyl)-4-ethyl-4-methyl-5-chloromethylene oxazoline hydrochloride prepared in the preceding step was dissolved in of 800 ml of methanol, 120 ml of water, and 75 ml of concentrated hydrochloric acid, warmed to 55° C. and stirred at that temperature for four hours. The crude reaction mixture was cooled down and poured into an ice/water slurry (1 liter) and then extracted with ethyl acetate (4×300 ml). The combined organic layers were washed with water (1×300 ml), then with 5% aqueous sodium bicarbonate (2×300 ml), and then with brine (1×300 ml) and dried. The solvent was then evaporated in the rotavap, yielding the crude product. The crude product was purified by trituration with 500 ml of a 10% ethyl ether:hexane mixture and filtered yielding 61.3 g (89% yield) of N-[3'-(1'-chloro-3'-methyl-2'-oxopentan)]-3-methoxyiminomethyl-5-chlorobenzamide(mp=90°-95° C.).

EXAMPLE 2

3-(3'-Methoxyiminomethylbenzamido)-1-chloro-3-methylbutan-2-one

This compound was prepared using essentially the same synthetic pathway as the compound of Example 1 using 3-methyl-1-pentyn-3-amine as starting material.

a) Preparation of 3-methyl-1-pentyn-3-amine

In a 2000 ml four-necked, round-bottomed flask fitted with a thermometer in a side-armed adapter connected to a scrubbing system, a mechanical stirrer, a 500 ml addition funnel and a bubbling tube connected to a lecture bottle of hydrogen chloride gas, were placed 350 ml of concentrated hydrochloric acid. This solution was cooled to 5° C. and hydrogen chloride gas was bubbled in until the size of the bubbles was constant. To this the alcohol was added over a time period of 2.5 hours at such a rate as to keep the temperature below 0° C. Simultaneously hydrogen chloride gas was bubbled through the reaction mixture. After the addition of the alcohol was complete, the resulting mixture was stirred at −5° C. for an additional 30 to 45 minutes. The resulting layers were separated and the organic layer was washed with ice-water until the pH of the washing liquids was 7. The resulting light yellow mobile oil was stored in the freezer until it was used in the following step without further purification.

b) Preparation of 3-amino-3-methyl-1-pentyne

In a 3000 ml, four-necked, round-bottomed flask fitted with a thermometer in a side-armed adapter connected to a scrubbing system, a mechanical stirrer, a 500 ml addition funnel and a bubbling tube connected to a lecture bottle of ammonia, were placed 1000 ml of concentrated ammonia hydroxide. This solution was cooled to −5° C., and ammonia was bubbled in until the size of the bubbles was constant. To this the chloride (600 g) and the 50% NaOH were charged in the addition funnels and added to the ammonia solution at such a rate that equal stoichiometric amounts of each compound were introduced in the reaction flask and the temperature was kept below 0° C. The addition took 2 to 3 hours. After the addition was complete, the reaction mixture was stirred 1 hour at −5° C. The work of this reaction was carried out as follows:

The two phases were separated and the organic phase was washed once with ice-water. The light yellow oil obtained was codistilled with water at atmospheric pressure. Four fractions were separated:

fraction 1 (bp 71° to 79° C.) was amine plus low boiling olefins, fractions 2 and 3 (bp 80° to 85° C.) were pure amine by 1H-NMR, and fraction 4 (bp 90° to 99° C.) was a mixture of the amine and the starting alcohol.

Fractions 1 and 4 were combined dissolved in dry ether and hydrogen chloride gas bubbled in while cooling. In this way 90 g of the pure amine hydrochloride were obtained. Total yield from the alcohol was 57%.

EXAMPLE 3

3-(3'-Ethoxyiminomethylbenzamido)-1-chloro-3-methylbutan-2-one

This compound was prepared using essentially the same synthetic pathway as the compound of Example 1 using ethoxylamine hydrochloride as starting material.

EXAMPLE 7

3-(3'-carboxymethylmethoxyiminomethylbenzamido)-1-chloro-3-methylbutan-2-one This compound was prepared using essentially the same synthetic pathway as the compound of Example 1 using aminoxyacetic acid methyl ester hydrochloride as starting material.

EXAMPLE 8

3-(3'-t-butoxyiminomethylbenzamido)-1-chloro-3-methylbutan-2-one

This compound was prepared using essentially the same synthetic pathway as the compound of Example 1 using t-butoxyamine hydrochloride as starting material.

EXAMPLE 9

N-[3'-(1'-chloro-3'-methyl-2'-oxopentan)]-3-chloro-5-methoxyiminomethylbenzamide a) Preparation of 3-Chloro-5-methylbenzoic acid In a 1 liter 3-necked round-bottomed flask equipped with gas dispersion tube, air stirrer and thermometer were placed 245 g (1.75 mole) of 5-chloro-m-xylene, 11.0 g (0.044 mole) of cobalt diacetate tetrahydrate, 4.6 g (0.044 mole) of sodium bromide and 320 ml of glacial acetic acid. The resulting mixture was warmed to 85° C. and air was bubbled slowly into the mixture for 40–45 hours. The reaction mixture was poured in 2 liters of a 1:1 mixture of ethyl acetate:water and the two layers were separated. The aqueous layer was extracted with ethyl acetate (1×500 ml) and the combined organic layers were washed with water (3×300 ml) and extracted with 2 liters 4% aqueous sodium hydroxide, followed by extraction with 1 liter 2% aqueous sodium hydroxide. Both basic solutions were kept separated and were independently acidified (concentrated hydrochloric acid), extracted with ethyl acetate (3×300 ml). The combined organic layers were washed with water (1×300 ml), dried and evaporated.

The 2% aqueous sodium hydroxide solution contained only the expected 3-chloro-5-methylbenzoic acid (88.2 g). The 4% aqueous sodium hydroxide solution yielded 123.6 g of a mixture that contained 65% of the expected 3-chloro-5-methylbenzoic acid. This mixture was dissolved in 875 ml of 2% aqueous sodium hydroxide and extracted with ethyl acetate (3×300 ml). The combined organic layers were washed with water (1×300 ml) and dried. The solvent was then evaporated yielding another 59 g of 3-chloro-5-methylbenzoic acid of 94% purity. These two solids were combined and used without further purification in the next step.

b) Preparation of Methyl-3-chloro-5-methylbenzoate 147.2 g (0.86 mole) of 3-chloro-5-methylbenzoic acid previously prepared were suspended in 250 ml of methanol and warmed up to 35° C. with stirring. To the resulting suspension were added slowly 113 g (0.95 mole) of thionyl chloride keeping the temperature below 60° C. (cooling by ice bath). When addition was completed, the resulting mixture was refluxed for 1 hour, then stirred and cooled down to room temperature. The solvent was removed in the rotovap and the residue poured into water. The resulting aqueous suspension was extracted with ethyl ether (2×750 ml). The combined organic extracts were washed with 2% aqueous sodium hydroxide (3×150 ml), followed by water (1×200 ml), and then brine (1×200 ml), dried over anhydrous sodium sulfate and then concentrated in the rotavap to give the expected Methyl-3-chloro-5-methylbenzoate (154.6 g, 97% purity), used as such in the next step.

c) Preparation of Methyl-3-Bromomethyl-5-chlorobenzoate 154.6 g (0.84 mole) of the previously prepared ester and 1.54 g of benzoyl peroxide were dissolved in 720 ml of carbon tetrachloride and refluxed for 2 hours using a Dean Stark apparatus to remove moisture. The heating was continued at gentle reflux and 112 g (0.63 mole) of N-bromosuccinimide were added in 5 to 22.5 g portions at 25 minute intervals with stirring. When addition was completed, the reaction mixture was refluxed for 30 minutes longer. At the end of this time analysis by gas chromatography showed 38% of starting material, 49% of the expected product, with the remainder being dibromo derivatives and other impurities. The reaction mixture was cooled down to room temperature and filtered through a silica gel bed. The resulting organic solution was washed with concentrated sodium thiosulfate (2×250 ml), dried with anhydrous sodium sulfate and concentrated to give 193.9 g of crude product. The product was isolated by distillation under vacuum. The expected product was distilled at 129°–135° C. at 0.5 mm of mercury. In this way were obtained 101.9 g of approx. 88% pure of methyl-3-bromomethyl-5-chlorobenzoate.

d) Preparation of Methyl-3-Acetoxymethyl-5-chlorobenzoate

In a 2 liter flask, 101.9 g (approx. 0.34 mole) of methyl-3-bromomethy-5-chlorobenzoate bromomethyl derivative and 100.2 g (1.02 mole) of potassium acetate in 460 ml of glacial acetic acid were combined and refluxed for 5 hours. The mixture was then cooled down to room temperature, poured into 3 liters of water and then extracted with ethyl ether (2×700 ml). The combined organic layers were washed with water (3×350 ml), then with 2% aqueous sodium hydroxide (5×300 ml) and then with brine (1×300 ml), dried over anhydrous sodium sulfate and concentrated in a rotavap to give 90.9 g of crude methyl-3-acetoxymethyl-5-chlorobenzoate product, used as such in the next step.

e) Preparation of 3-Chloro-5-hydroxymethylbenzoic acid

In a 1 liter flask were dissolved 74.0 g (1.12 mole) of 85% KOH in 0.45 liter of methanol and warmed up to 60° C. The preceding acetoxy derivative (90.9 g) was added and heated with stirring at 60° C. for 3 hrs. The reaction mixture was cooled down to room temperature and the solvent eliminated in the rotavap. The resulting oil was dissolved in 1 liter of water, washed with ethyl ether (1×500 ml). The aqueous layer was made acidic with concentrated hydrochloric acid. The resulting acidic suspension was extracted with ethyl ether (3×350 ml). The combined organic extracts were washed with water (2×500 ml) and then with brine (2×300 ml), dried over anhydrous sodium sulfate and concentrated in the rotavap to give 71.5 g of expected 3-chloro-5-hydroxymethylbenzoic acid as a white solid.

f) Preparation of 5-chloroisophthalic acid

In a 5 liter 3-necked round-bottomed flask equipped with mechanical stirrer, condenser, nitrogen inlet and thermometer were placed 5-chloro-m-xylene (112 g, 0.8 mole), water (840 ml) and 2-methyl-2-propanol (1200 ml). The resulting solution was warmed up to 70° C. and solid potassium permanganate (50 g) was added. The reaction was refluxed until the purple color was gone; the reaction mixture was then cooled down to 70° C. and another portion (50 g) of potassium permanganate was added and the reaction mixture refluxed until the purple color was gone. In this way a total of 700 g of potassium permanganate was added. After the color of the last addition of potassium permanganate was gone, the reaction mixture was cooled down to approximately 35°–40° C. and filtered through celite. The manganese dioxide cake was washed several times with 2% aqueous sodium hydroxide, the combined filtrates were made acidic with concentrated hydrochloric acid and extracted with ethyl acetate (5×500 ml). The combined organic layers were washed with water (3×500 ml), dried over magnesium sulfate and concentrated in a rotavap yielding 5-chlorophthalic acid as a white solid (134.5 g).

g) Preparation of 5-chloroisophthalic acid dimethyl ester

In a 2 liter 3-necked round-bottomed flask were placed 5-chloroisophthalic acid (144.6 g) and methanol (700 ml). The resulting solution was warmed up to 60° C. and thionyl chloride (189 g) was added dropwise with vigorous stirring. After the addition was complete, the reaction mixture was refluxed 1.5 hours longer. The solvent was then removed in the rotavap. The residue was dissolved in ethyl ether (1 liter), the solution was then washed sequentially with water (3×300 ml), 2% aqueous sodium hydroxide (3×200 ml) and then water (2×200 ml), dried over magnesium sulfate and concentrated in a rotavap yielding 5-chloroisophthalic acid dimethyl ester as a white solid (146.4 g).

h) Preparation of 5-chloroisophthalic acid monomethyl ester

In a 5 liter 3-necked round-bottomed flask were placed 5-chloroisophthalic acid dimethyl ester (146.4 g) and methanol (2.5 liters). To the resulting solution was added (dropwise) a solution of potassium hydroxide (42.8 g) in methanol (500 ml) with vigourous stirring under nitrogen. The resulting mixture was refluxed 2 hours, cooled down and the solvent was then eliminated in the rotavap. The residue was taken up in water (800 ml), the pH brought to 8 and the resulting solution washed with ethyl ether. The aqueous solution was made acidic with aqueous hydrochloric acid and extracted with ethyl acetate (3×400 ml). The combined organic layers were dried (magnesium sulfate) and the solvent was then eliminated in the rotavap. The solid residue was stirred in 1.3 liters of chloroform overnight and filtered. The solvent was then evaporated yielding 5-chloroisophthalic acid monomethyl ester as a white solid (29 g).

i) Preparation of 3-chloro-5-hydroxymethyl benzoic acid methyl ester

In a 3 liter 3-necked round-bottom flask equipped with mechanical stirrer and nitrogen inlet was placed 5-chloroisophthalic acid monomethyl ester (29.4 g). Borane tetrahydrofuran complex in tetrahydrofuran solution (1M, 280 ml) was then added to the flask dropwise at room temperature. The resulting solution was stirred at room temperature overnight. The reaction mixture was poured into saturated aqueous ammonium chloride solution (750 ml) and extracted with ethyl acetate (3×500 ml). The combined organic layers were agitated with 2% aqueous hydrochloric acid, washed with water, dried and the solvent eliminated in the rotavap yielding 29.4 g of 3-chloro-5-hydroxymethyl benzoic acid methyl ester as a clear oil.

j) Preparation of 3-chloro-5-hydroxymethyl benzoic acid

The previous ester was mixed together with potassium hydroxide (10.1 g) and methanol (500 ml). The resulting mixture was refluxed during 3 hours then cooled down to room temperature, the solvent removed in the rotavap and the residue taken up in water (150 ml). The aqueous solution was washed with ethyl ether (2×75 ml), acidified with hydrochloric acid, and extracted with ethyl acetate (3×100 ml). The combined organic layers were washed with water and dried with magnesium sulfate. The solvent was eliminated in he rotavap, yielding 3-chloro-5-hydroxymethylbenzoic acid as a white solid (23.1 g).

k) Preparation of 3-formyl-5-chlorobenzoic acid

In a 2 liter 4-necked round-bottomed flask were placed 500 ml of methylene chloride and cooled down to −78° C. 44.6 g (0.35 mole) of oxalyl chloride were added slowly, followed by dropwise addition of 57.7 g (0.74 mole) of dry dimethylsulfoxide in 40 ml of methylene chloride, keeping the temperature below −70° C. After the addition was completed, the reaction mixture was stirred at −78° C. for 30 minutes and 71.5 g (0.38 mole) of the previously prepared 3-chloro-5-hydroxymethylbenzoic acid were added in 1 portion and 60 ml more of methylene chloride followed by dropwise addition of 149.5 g (1.48 mole) of triethylamine, keeping the temperature below −65° C. The reaction mixture was then warmed up slowly to room temperature and stirred during 90 minutes and washed with 2% aqueous sodium hydroxide (4×500 ml). The combined basic layers were washed with hexane once, then acidified with concentrated hydrochloric acid and then extracted with ethyl acetate (4×500 ml). The combined organic layers were washed with water (1×500 ml) and then with brine (1×300 ml) and dried over anhydrous magnesium sulfate. The solvent was then eliminated in a rotavap, yielding 52 g of 3-formyl-5-chlorobenzoic acid.

l) Preparation of 3-formyl-5-chlorobenzoyl chloride

A mixture of 3-formyl-5-chlorobenzoic acid (66.5 g, 0.36 moles), thionyl chloride (51.5 g, 0.43 moles), and dimethylformamide (1 ml), in toluene (400 ml) was slowly warmed to 70° C. and stirred at that temperature for 2 hours. The toluene was eliminated in the rotavap to yield 3-formyl-5-chlorobenzoyl chloride, used in the next step as such.

m) Preparation of N-(3-Methylpent-1-yne)-3-chloro-5-methoxyiminomethylbenzamide

To a cooled, well stirred mixture of 3-methyl-1-pentyn-3-amine hydrochloride (47.2 g, 0.354 moles), and dimethylformamide (74 ml) was added dropwise triethylamine (71.5 g, 0.71 mole) over 30 minutes. When the addition was completed, the resulting mixture was stirred another 30 minutes at 0° C. To the resulting mixture was added dropwise a solution of 3-formyl-5-chlorobenzoyl chloride (74 g, approx. 0.36 mole) dissolved in tetrahydrofuran (65 ml), keeping the temperature between 5° to 10° C. When the addition was completed, the resulting mixture was stirred another 6 hours at room temperature. To the well stirred mixture were added dropwise a solution of methoxylamine hydrochloride (30.7 g, 0.369 mole) in dimethylformamide (165 ml) at room temperature, followed by the dropwise addition of triethylamine (37.2 g, 0.369 mole), all the while keeping the temperature below 20° C. The resulting mixture was stirred overnight at room temperature. The reaction mixture was poured into ice-water (1 liter) and extracted with ethyl acetate (3×400 ml). The combined organic layers were washed with water (2×300 ml), then with 5% aqueous sodium bicarbonate (2×300 ml) and then with brine (1×400 ml) and then dried over anhydrous sodium sulfate. The solvent was then eliminated in a rotavap yielding 69.3 g of N-(3-methylpent-1-yne)-3-methoxyiminomethyl-5-methylbenzamide, used as such in the next step.

n) Preparation of 2-(3'-chloro-5'-methoxyiminomethylphenyl)-4-ethyl-4-methyl-5-chloromethylene oxazoline hydrochloride In a 2 liter, three-necked, round-bottomed flask fitted with a mechanical stirrer, a thermometer and a 500 ml addition funnel were dissolved 69.3 g, 0.237 moles, of N-(3-methylpent-1-yne)-3-chlorol-5-methoxyiminomethybenzamide in a mixture of 500 ml of methylene chloride and 500 ml of hexane. The resulting mixture was cooled down to −50° C. and a cold chlorine solution in methylene chloride (17.4 g of chlorine in 500 ml of a 1:1 mixture of methylene chloride and hexane) was added very slowly. When the addition was completed, the reaction mixture was stirred at −65° C. during 30 minutes and then warmed up slowly to room temperature and washed with water (1×110 ml). The solvent was then evaporated in the rotavap, yielding 173.2 g (85%) 2-(3'-chloro-5'-methoxyiminomethylphenyl)-4-ethyl-4-methyl-5-chloromethylene oxazoline hydrochloride as a viscous oil which was used as such in the next step.

o) Preparation of N-[3'-(1'-chloro-3'-methyl-2'-oxopentan)]-3-chloro-5-methoxyiminomethylbenzamide 73.2 g (0.2 moles) of 2-(3'-chloro-5'-methoxyiminomethylphenyl)-4-ethyl-4-methyl-5-chloromethylene oxazoline hydrochloride prepared in the preceding step were dissolved in 800 ml of tetrahydrofurane, 110 ml of water, and 35 ml of concentrated hydrochloric acid, warmed up to 55° C. and stirred at that temperature for four hours. The crude reaction mixture was concentrated down to a slurry and partitioned between ethyl acetate and water. The aqueous layer was extracted with ethyl acetate and the combined organic layers were washed with water (1×300 ml), then with 5% aqueous sodium bicarbonate (2×300 ml) and then with brine (1×300 ml) and dried. The solvent was then evaporated in the rotavap yielding 74.3 g of crude product, which was purified by column chromatography, yielding 41.9 g N-[3'-(1'-chloro-3'-methyl-2'-oxopentan)]-3-chloro-5-methoxyiminomethylbenzamide as a white solid.

EXAMPLE 10

3-(4'-Methoxyiminomethylbenzamido)-1-chloro-3-methylpentan-2-one

This compound was prepared using essentially the same synthetic pathway as the compound of Example 1 starting with 4-formylbenzoic acid.

EXAMPLE 12

N-[3'-(1'-chloro-3'-methyl-2'-oxopentan)]-3-methoxyiminomethyl-5-methylbenzamide a) Preparation of Methyl, 3,5-dimethylmethylbenzoate 500 g (3.33 mole) of 3,5-dimethylbenzoic acid was suspended in 1 liter of methanol and warmed up to 35° C. with stirring. To the resulting suspension were slowly added 436 g (3.67 mole) of thionyl chloride, keeping the temperature below 60° C. (cooling by ice bath). When addition was completed, the resulting mixture was refluxed for 1 hour, then stirred and cooled down to room temperature. The solvent was removed in the rotovap and the residue poured into water. The resulting aqueous suspension was extracted with ethyl ether (2×750 ml). The combined organic extracts were washed, first with 5% aqueous sodium bicarbonate (2×350 ml), followed by water (1×350 ml), and then brine (1×250 ml), dried over anhydrous sodium sulfate and then concentrated in the rotavap to give (516.2 g, 94.5%) as a straw colored oil used as such in the next step.

b) Preparation of Methyl-3-Bromomethyl-5-methylbenzoate 361 g (2.2 mole) of the previously prepared ester and 3.5 g (0.014 mole) of benzoyl peroxide were dissolved in 1.7 liter of CCl$_4$ and refluxed for 2 hours using a Dean Stark apparatus to remove moisture. The heating was continued at gentle reflux and 300 g (1.685 mole) of N-bromosuccinimide were added in 10 to 30 g portions at 10–15 min intervals with stirring. When addition was completed, the reaction mixture was refluxed for 30 minutes longer. At the end of this time analysis by gas chromatography showed 29% of starting material, 58% of the expected product with the remainder being dibromo derivatives and other impurities. The reaction mixture was cooled down to room temperature and filtered through a silica gel bed. The resulting organic solution was washed with concentrated sodium thiosulfate (2×250 ml), dried with anhydrous sodium sulfate and concentrated to give 502.3 g (94% yield) of crude product. The product was isolated by distillation under vacuum (the expected product was distilled at 110°–16° C./0.5 mm of mercury). In this way were obtained 187.3 g of methyl-3-Bromomethyl-5-methylbenzoate of greater than 96% purity (35% yield).

c) Preparation of Methyl-3-Acetoxymethyl-5-methylbenzoate

In a 5 liter flask were combined 507 g (2.09 mole) of methyl-3-bromomethyl-5-methylbenzoate with 615 g (6.3 mole) of potassium acetate in 2850 ml of glacial acetic acid and refluxed for 3 hours. The contents of the flask were then cooled down to room temperature and divided in 3 equal portions for work up. Each portion was poured into 2 liter of water and extracted with ethyl ether (3×300 ml). The combined organic layers were washed with water (3×600 ml) and then with 2% aqueous sodium hydroxide (5×200 ml) and then dried over sodium sulfate. The solvent was then eliminated in the rotavap to give 420.8 g (90% yield) of crude product, used as such in the next step.

d) Preparation of 3-Hydroxymethyl-5-methylbenzoic acid

In a 5 liter flask were dissolved 380 g (5.77 mole) of 85% KOH in 2.2 liter of methanol and warmed up to 60° C. The methyl-3-acetoxymethyl-5-methylbenzoate from the previous step was added and heated with stirring at 60° C. for 2.5 hrs. The reaction mixture was cooled down to room temperature and the solvent eliminated in the rotavap. The resulting oil was dissolved in 1.5 liter of water and then washed with ethyl ether (1×1 liter). The aqueous layer was made acidic with concentrated hydrochloric acid and the resulting acidic suspension was extracted with ethyl acetate (3×350 ml). The combined organic extracts were then washed with water (2×600 ml) and then brine (2×500 ml), dried over sodium sulfate and concentrated in the rotavap to give 287.6 g of 3-hydroxymethyl-5-methylbenzoic acid.

e) Preparation of 3-formyl-5-methylbenzoic acid

In a 1 liter 4-necked round-bottomed flask were placed 500 ml of methylene chloride and cooled down to −78° C. 41.3 g (0.33 mole) of oxalyl chloride were added slowly, followed by dropwise addition of 56.4 g (0.72 mole) of dry dimethylsulfoxide in 30 ml of methylene chloride, all the while keeping the temperature below −70° C. After the addition was completed the reaction mixture was stirred at −78° C. for 30 minutes and 60 g (0.36 mole) of the previously prepared 3-hydroxymethyl-5-methylbenzoic acid were added in 1 portion, followed by dropwise addition of 131.4 g (1.3 mole) of triethylamine, keeping the temperature below −65° C. during each of the additions. The reaction mixture was then warmed up slowly to room temperature, stirred for 90 minutes and then washed with 2% aqueous sodium hydroxide (3×500 ml). The combined basic layers were washed with hexane once and acidified with concentrated hydrochloric acid and then extracted with ethyl acetate (4×500 ml). The combined organic layers were washed with water (1×500 ml) and then with brine (1×300 ml) and dried over anhydrous magnesium sulfate. The solvent was then eliminated in a rotavap. The resulting oily product was triturated with hexane and filtered yielding 52 g (88%) 3-formyl-5-methylbenzoic acid as a tan solid.

f) Preparation of 3-formyl-5-methylbenzoyl chloride

A mixture of 3-formyl-5-methylbenzoic acid (75.0 g, 0.457 moles), thionyl chloride (65 g, 0.0547 moles), and dimethylformamide (1 ml), in toluene (500 ml) was slowly warmed to 70° C. and stirred at that temperature for 2 h. The toluene was eliminated in a rotavap to yield 3-formyl-5-methylbenzoic chloride used in the next step as such.

g) Preparation of N-[3'-(3'-methyl-1'-pentynyl)]-3-methoxyiminomethyl-5-methylbenzamide To a cooled, well stirred mixture of 3-methyl-1-pentyn-3-amine hydrochloride (64 g, (0.472 moles)), and dimethylformamide (140 ml) was added dropwise triethylamine (90 g, 0.89 mole) over 30 minutes. Stirring was continued for another 30 minutes at 0° C. following completion of the addition. To the resulting mixture was added dropwise a solution of 3-formyl-5-methylbenzoyl chloride (82 g, 0.45 mole) dissolved in tetrahydrofurane (90 ml), keeping the temperature between 5° to 10° C. When the addition was complete, the resulting mixture was stirred for another 6 hours at room temperature. To the well stirred mixture was added dropwise a solution of methoxylamine hydrochloride (38.4 g, 0.46 mole) in dimethylformamide (200 ml) at room temperature, followed by the dropwise addition of triethylamine (45 g) while keeping the temperature below 20° C. The resulting mixture was stirred overnight at room temperature. The reaction mixture was poured into ice-water (900 ml) and extracted with ethyl acetate (3×300 ml). The combined organic layers were washed with water (3×400 ml), then with 5% aqueous sodium bicarbonate (2×400 ml) and then with brine (1×400 ml) and then dried over anhydrous sodium sulfate. The solvent was then eliminated in a rotavap yielding 110.1 g of N-[3'-(-3'-methyl-1'-pentynyl)]-3-methoxyiminomethyl-5-methylbenzamide used as such in the next step.

h) Preparation of 2-(3'-chloro-5'-methoxyiminomethylphenyl)-4-ethyl-4-methyl-5-chloromethylene oxazoline hydrochloride In a 2 liter, three-necked, round-bottomed flask fitted with a mechanical stirrer, a thermometer and a 500 ml addition funnel were dissolved 100 g, 0.367 moles of N-[3'-(3'-methyl-1'-pentynyl)]-3-methoxyiminomethyl-5-methylbenzamide in a mixture of 350 ml of methylene chloride and 350 ml of hexane. The resulting mixture was cooled down to −50° C. and a cold chlorine solution in methylene chloride (26 g of chlorine in 648 g of methylene chloride) was added very slowly. When the addition was completed, the reaction mixture was stirred at −65° C. during 30 minutes and warmed up slowly to room temperature and washed with water (2×300 ml). The solvent was then evaporated in the rotavap yielding 104.1 g (82.6%) 2-(3'-chloro-5'-methoxyiminomethylphenyl)-4-ethyl-4-methyl-5-chloromethylene oxazoline hydrochloride as a light yellow solid which was used as such in the next step.

i) Preparation of N-[3'-(1'-chloro-3'-methyl-2'-oxopentan)]-3-methoxyiminomethyl-5-chloro-benzamide 104.0 g (0.303 moles), of 2-(3'-chloro-5'-methoxyiminomethylphenyl)-4-ethyl-4-methyl-5-chloromethylene oxazoline hydrochloride prepared in the preceding step was dissolved in 1 liter of tetrahydrofuran, 160 ml of water, and 36 ml of concentrated hydrochloric acid, warmed up to 55° C. and stirred at that temperature during four hours. The crude reaction mixture was cooled down and poured into ice/water slurry (1 liter) and then extracted with ethyl acetate (4×300 ml). The combined organic layers were washed with water (1×300 ml), then with 5% aqueous sodium bicarbonate (2×300 ml), and then with brine (1×300 ml) and then dried. The solvent was then evaporated in the rotavap yielding 104.3 g of the crude product, which was purified by dissolving it in 120 ml of hot ethyl acetate and then filtered the hot solution. To the filtrate was slowly added 240 ml of hexane, giving a cloudy solution which crystallized upon cooling to yield (81.9 g) N-[3'-(1'-chloro-3'-methyl-2'-oxopentan)]-3-methoxyiminomethyl-5-chlorobenzamide.

EXAMPLE 4

3-(3'-Ethoxyiminomethylbenzamido)-1,1-dichloro-3-methylbutan-2-one

EXAMPLE 5

3-(3'-Methoxyiminomethylbenzamido)-1,1-dichloro-3-methylpentan-2-one

EXAMPLE 6

3-(3'-carboxymethylmethoxyiminomethylbenzamido)-1,1-dichloro-3-methylbutan-2-one and

EXAMPLE 11

N-[3'-(1',1'-dichloro-3'-methyl-2'-oxopentan)]-3-methoxyiminomethyl-5-methylbenzamide The compounds of Examples 4, 5, 6 and 11 were isolated as subproducts of the respective chlorination steps of the above described processes for synthesizing the compounds of Examples 3, 1, 7 and 12, respectively.

EXAMPLE 13

N-[3'-(1'-thiocyano-3'-methyl-2'oxopentan)]-3-methoxyiminomethylbenzamide

The compound of Example 1, i.e. 1-3-(3'-methoxyiminomethylbenzamido)-1-chloro-3-methylpentan-2-one, (2.0 g, 0.0064 mole) was mixed with potassium thiocyanate (1.6 g, 0.016 mole) in acetone (40 ml). The resulting mixture was stirred for 12 hours at room temperature under nitrogen. The reaction mixture was then poured into water (150 ml) and extracted with ethyl acetate (3×75 ml). The combined organic layers were washed with saturated aqueous ammonium chloride (3×50 ml) and dried (anhydrous magnesium sulfate). The solvent was then eliminated in a rotavap. The crude product was purified by column chromatography yielding 560 mg of N-[3'-(1'-thiocyano-3'-methyl-2'-oxapentan)]-3-methoxyiminomethylbenzamide.

EXAMPLE 14

N-[3'-(1'-chloro-3'-methyl-2'-oxopentan)]-4-chloro-3-methoxyiminomethylbenzamide This compound was prepared using essentially the same synthetic pathway as the compound of Example 12 using 4-chloro-3-methylbenzoic acid as the starting material.

EXAMPLE 15

N-[3'-(1'-chloro-3'-methyl-2'-oxopentan)]-3,5-dimethoxyiminomethylbenzamide

This compound was prepared using essentially the same synthetic pathway as set forth in Example 1 using 3,5-dimethylbenzoic acid as the starting material.

EXAMPLE 16

N-[3'-(1'-chloro-3'-methyl-2'-oxopentan)]-3-chloro-4-methoxyiminomethylbenzamide This compound was prepared using essentially the same synthetic pathway as the compound of Example 12 using 3-chloro-4-methylbenzoic acid as the starting material.

EXAMPLE 17

3-(3'-Methoxyiminomethyl(methyl)benzamido)-1-chloro-3-methylpentan-2-one

This compound was prepared using essentially the same synthetic pathway as the compound of Example 1 using 3-acetylbenzoic acid as the starting material.

EXAMPLE 18

3-(3'-Hydroxyiminomethylbenzamido)-1-chloro-3-methylbutan-2-one

This compound was prepared using essentially the same synthetic pathway as the compound of Example 1 using hydroxylamine hydrochloride as the starting material.

EXAMPLE 19

3-(4'-Methoxyiminomethyl(methyl)benzamido)-1-chloro-3-methylpentan-2-one

This compound was prepared using essentially the same synthetic pathway as the compound of Example 1 using 4-acetylbenzoic acid as the starting material.

EXAMPLE 20

N-[3'-(1'-chloro-3'-methyl-2'-oxopentan)]-3,5-dichloro-4-methoxyiminobenzamide a) Preparation of 3,5-dichloro-4-methylbenzoic acid To a solution of p-toluic acid (95.0 g, 0.698 mole) in methylene chloride (1 liter), was added aluminum chloride (260.0 g, 1.948 mole) portionwise keeping the reaction temperature below 10° C. (ice-water bath). When the addition was completed (approx. 30 minutes) chlorine gas was bubbled in at such a rate as to keep the temperature below 10° C. The reaction was followed by gas-liquid chromatography. After about 4 hours, most of the starting material had been converted to the expected compound. The resulting mixture was poured into ice and concentrated hydrochloric acid and then extracted with ethyl acetate several times. The combined organic layers were then washed with water and dried over anhydrous sodium sulfate. Removing the solvent in a rotavap yielded the crude product as a white solid. Recrystallization from acetone/water or ethyl acetate/hexane yielded 3,5-dichloro-4-methylbenzoic acid with minor impurities 115.4 g (81% yield of product).

b) Preparation of 4-bromomethyl-3,5-dichlorobenzoic acid 99 g (0.48 mole) of the previously prepared 3,5-dichloro-4-methylbenzoic acid and 0.5 g (0.002 mole) of benzoyl peroxide were dissolved in 800 ml of CCl4 and refluxed for 2 hours using a Dean Stark apparatus to remove moisture. The heating was continued at gentle reflux and 94 g (0.53 mole) of N-bromosuccinimide were added in 10×9.4 g portions at 10–15 min intervals with stirring. When addition was completed, the reaction mixture was refluxed for 30 minutes longer. At the end of this time analysis by gas chromatography showed 3% of starting material, 94% of the expected product and the rest dibromo derivatives and other impurities. The reaction mixture was cooled down to room temperature and filtered. The resulting organic solution was washed with concentrated sodium thiosulfate (2×250 ml), dried with anhydrous sodium sulfate and concentrated to give 47.2 g of an oily residue, which was mostly the expected compound. The solid was also the expected 4-bromomethyl-3,5-dichlorobenzoic acid contaminated with succinimide. The solid was slurried in 1 liter of water for 1 hour, filtered and then dried. This yielded another 89.0 g of 4-bromomethyl-3,5-dichlorobenzoic acid.

c) Preparation of 4-acetoxymethyl-3,5-dichlorobenzoic acid

In a 1 liter flask were combined 94 g (0.33 mole) of the bromomethyl derivative prepared previously with 112 g (1.143 mole) of potassium acetate in 500 ml of glacial acetic acid and were refluxed during 3 hours. At the end of this time the reaction was complete. The reaction mixture was cooled down and the solution was separated from the solids. The acetic acid solution was reduced in volume and combined with solids into 1 liter of water. The resulting aqueous solution was extracted with ethyl acetate (3×300 ml). The combined organic layers were washed with water (2×250 ml) and then with brine (1×250 ml), dried over sodium sulfate and concentrated to give 67.7 g 4-acetoxymethyl-3,5acid, used as such in the next step.

d) Preparation of 3,5-dichloro-4-hydroxymethylbenzoic acid

In a 1 liter flask were dissolved 17.2 g (0.26 mole) of 85% KOH in 400 ml of methanol and warmed up to 65° C. The previously prepared acetoxy derivative was added slowly and heated with stirring at 60° C. for 2.5 hours. The reaction mixture was cooled down and the solvent removed in the rotavap. The residue was dissolved in water and washed with ethyl ether (2×250 ml) and acidified with concentrated hydrochloric acid. The solid so formed was separated by filtration and after drying yielded 52.5 g (99% purity) 4-hydroxymethyl-3,5-dichlorolbenzoic acid.

e) Preparation of 4-formyl-3,5-dichlorobenzoic acid

In a 1 liter 4-necked round-bottomed flask were place 300 ml of methylene chloride and cooled down to −78° C. 26.0 g (0.20 mole) of oxalyl chloride were added slowly, followed by dropwise addition of 35.4 g (0.452 mole) of dry dimethylsulfoxide in 25 ml of methylene chloride, keeping the temperature below −70° C. After the addition was completed the reaction mixture was stirred at −78° C. for 30 minutes and 50.0 g (0.226 mole) of 4-hydroxymethyl-3,5-dichlorobenzoic acid were added in 1 portion 82.5 g (0.817 mole) of triethylamine in 25 ml of methylene chloride were added dropwise, keeping the temperature below −65° C. The reaction mixture was warmed up slowly to room temperature and stirred during 90 minutes, washed with 2% aqueous sodium hydroxide (3×300 ml). The combined basic layers were washed with hexane (2×250 ml) then acidified with concentrated hydrochloric acid and then extracted with ethyl acetate (4×200 ml). The combined organic layers were washed with water (1×500 ml), and then with brine (1×300 ml) and dried over anhydrous magnesium sulfate. The solvent was then eliminated in a rotavap. The resulted oily product was triturated with hexane and filtered yielding 39.6 g (80% purity) 4-formyl-3,5-dichloro benzoic acid as a tan solid.

f) Preparation of 4-formyl-3,5-dichlorobenzoyl chloride

A mixture of 4-formyl-3,5-dichlorobenzoic acid (15.0 g, 0.06 moles), thionyl chloride (12.1 g, 0.107 moles), and dimethylformamide (5 ml) in toluene (100 ml) was slowly warmed to 70° C. and stirred at that temperature for 2 hours. The toluene was eliminated in the rotavap to yield 16.5 g of 4-formyl-3,5-dichlorobenzoyl chloride used in the next step as such.

g) Preparation of N-[3'-(3'-methyl-1'-pentynyl)]-4-formyl-3,5-dichlorobenzamide

To a suspension of 11.4 g (0.18 mole) of 3-methyl-1-pentyn-3-aminohydrochloride in 150 ml of ethyl ether were added 72 g (0.18 mole) of 10% aqueous sodium hydroxide with stirring at 5° to 10° C. When the addition was completed, the reaction mixture was warmed slowly to room temperature and 16.5 g (0.0695 mole) of 4-formyl-3,5-dichlorobenzoyl chloride were slowly added. The reaction mixture was poured into 200 ml of water and extracted with ethyl ether (3×200 ml). The combined organic layers were washed with water (2×200 ml), then with brine (1×200 ml) and dried over anhydrous sodium sulfate, yielding the expected compound contaminated with 4-hydroxymethyl-3,5-dichlorobenzamide. A portion of the aldehyde derivative was purified by chromatographic column (Silica gel/mixture of ethyl acetate-hexane 10% to 100% ethyl acetate) yielding 9.7 g N-[3'-(3'-methyl-1'-pentynyl)]-4-formyl-3,5-dichlorobenzamide as a white solid.

h) Preparation of N-[3'-(3'-methyl-1'-pentynyl)]-4-methoxyimino-3,5-dichlorobenzamide To 3.3 g (0.011 mole) of N-[3'-(3'-methyl-1'-pentynyl)]-4-formyl-3,5-dichlorobenzamide in 50 ml of methylene chloride were added 1.29 g (0.015 mole) of methoxylamine hydrochloride and 2.2 ml (0.0015 mole) of triethylamine hydrochloride with stirring at 0° C. A precipitate immediately formed. The reaction mixture was warmed to room temperature and stirred overnight. The reaction mixture was poured into water (100 ml) and then extracted with ethyl ether (3×25 ml). The combined organic layers were washed with water (2×30 ml) and then dried over sodium sulfate. The solvent was then evaporated, yielding 3.0 g of N-[3'-(3'- methyl-1'-pentynyl)]-4-methoxyimino-3,5-dichlorobenzamide as a white solid.

characterizing each of the exemplary compounds is set forth in Table 2.

TABLE 1

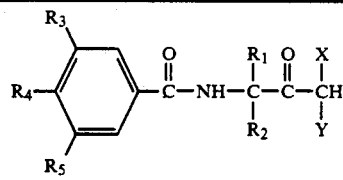

| Ex. No. | R1 | R2 | R3 | R4 | R5 | X | Y |
|---------|----|----|-----|----|----|---|---|
| 1 | C$_2$H$_5$ | CH$_3$ | CH=NOCH$_3$ | H | H | Cl | H |
| 2 | CH$_3$ | CH$_3$ | CH=NOCH$_3$ | H | H | Cl | H |
| 3 | C$_2$H$_5$ | CH$_3$ | CH=NOCH$_2$CH$_3$ | H | H | Cl | H |
| 4 | C$_2$H$_5$ | CH$_3$ | CH=NOCH$_2$CH$_3$ | H | H | Cl | Cl |
| 5 | C$_2$H$_5$ | CH$_3$ | CH=NOCH$_3$ | H | H | Cl | Cl |
| 6 | C$_2$H$_5$ | CH$_3$ | CH=NOCH$_2$COOCH$_3$ | H | H | Cl | Cl |
| 7 | C$_2$H$_5$ | CH$_3$ | CH=NOCH$_2$COOCH$_3$ | H | H | Cl | H |
| 8 | C$_2$H$_5$ | CH$_3$ | CH=NOC(CH$_3$)$_3$ | H | H | Cl | H |
| 9 | C$_2$H$_5$ | CH$_3$ | CH=NOCH$_3$ | H | Cl | Cl | H |
| 10 | C$_2$H$_5$ | CH$_3$ | H | CH=NOCH$_3$ | H | Cl | H |
| 11 | C$_2$H$_5$ | CH$_3$ | CH=NOCH$_3$ | H | CH$_3$ | Cl | Cl |
| 12 | C$_2$H$_5$ | CH$_3$ | CH=NOCH$_3$ | H | CH$_3$ | Cl | H |
| 13 | C$_2$H$_5$ | CH$_3$ | CH=NOCH$_3$ | H | H | SCN | H |
| 14 | C$_2$H$_5$ | CH$_3$ | CH=NOCH$_3$ | Cl | H | Cl | H |
| 15 | C$_2$H$_5$ | CH$_3$ | CH=NOCH$_3$ | H | CH=NOCH$_3$ | Cl | H |
| 16 | C$_2$H$_5$ | CH$_3$ | Cl | CH=NOCH$_3$ | H | Cl | H |
| 17 | C$_2$H$_5$ | CH$_3$ | C(CH$_3$)=NOCH$_3$ | H | H | Cl | H |
| 18 | C$_2$H$_5$ | CH$_3$ | CH=NOH | H | CH$_3$ | Cl | H |
| 19 | C$_2$H$_5$ | CH$_3$ | H | C(CH$_3$)=NOCH$_3$ | H | Cl | H |
| 20 | C$_2$H$_5$ | CH$_3$ | Cl | CH=NOCH$_3$ | Cl | Cl | H | i) Preparation of 2-(3',5'-dichloro-4'-methoxyiminomethylphenyl)-4-ethyl-4-methyl-5-chloromethylene oxazoline hydrochloride In a 250 ml, three-necked, round-bottomed flask fitted with a mechanical stirrer, a thermometer and a 10 ml addition funnel were dissolved 2.0 g 0.0061 moles) of N-[3'-(3'-methyl-1'-pentynyl)]-4-methoxyimino-3,5-dichlorobenzamide in 100 ml of methylene chloride. The resulting mixture was cooled down to −50° C. and a cold chlorine solution in methylene chloride (4.15 ml, 1.48M) was added very slowly. When the addition was completed the reaction mixture was stirred at −65° C. during 30 minutes. The solvent was evaporated in the rotavap yielding 2-(3',5'-dichloro-4'-methoxyiminomethylphenyl)-4-ethyl-4-methyl-5-chloromethylene oxazoline hydrochloride as a light yellow solid which was used as such in the next step.

j) Preparation of N-[3'-(1'-chloro-3'-methyl-2'-oxopentan)]-3,5-dichloro-4-methoxyiminobenzamide 2.0 g, of 2-(3,5-dichloro-4-methoxyiminophenyl)-4-methyl-4-ethyl-5-chloromethylenyloxazoline hydrochloride prepared in the preceding step was dissolved in a mixture of 100 ml of methanol, 10 ml of water, and 5 ml of concentrated hydrochloric acid, warmed to 55° C. and stirred at that temperature for four hours. The crude reaction mixture was cooled down and poured into a mixture of ice and water, neutralized with saturated aqueous sodium bicarbonate and then extracted with methylene chloride (4×50 ml). The combined organic layers were washed with brine and then dried. The solvent was then evaporated in a rotavap yielding 2.0 g of the crude product, which was then purified by column chromatography yielding 350 mg of N-[3'-(1'-chloro-3'-methyl-2'-oxopentan)]-3,5-dichloro-4-methoxyiminobenzamide.

The substituent groups for the compounds of Examples 1 to 20 are set forth in Table 1 and NMR data

TABLE 2

| Example Number | 200 MHz, delta scale in ppm, Tetramethylsilane (TMS) standard, using CDCl$_3$ as solvent |
|---|---|
| 1 | 8.11(1, s), 8.00(1, s), 7.77(2, d), 7.48(1, t), 6.87(1, bs), 4.24(2, dd), 4.02(3, s), 2.53(3, s), 2.35–2.15(1, m), 2.05–1.85(1, m), 0.92(3, t) |
| 2 | 8.12(s), 8.02(1, s), 7.77(2, dd), 7.49(1, t), 6.74(1, bs), 4.44(2, dd), 4.03(3, s), 1.64(6, s) |
| 3 | 8.11(1, s), 7.99(1, s), 7.74(2, dd), 7.37(1, t), 6.85(1, bs), 4.41(2, dd), 4.24(2, q), 2.35–2.15(1, m), 2.05–1.85(1, m), 1.62(3, s), 1.43(3, t), 0.91(3, t) |
| 4 | 8.13(1, s), 8.01(1, s), 7.76(2, dd), 7.48(1, t), 6.77(1, bs), 6.56(1, s), 4.27(2, q), 2.35–2.2(1, m), 2.2–2.01(1, m), 1.72(5, s), 1.36(3, t), 0.97(3, t) |
| 5 | 8.13(1, s), 8.01(1, s), 7.78(2, dd), 7.49(1, t), 6.76(1, bs), 6.55(1, s), 4.02(3, s), 2.3–2.1(1, m), 2.1–1.9(1, m), 1.73(3, s), 0.98(3, t) |
| 6 | 8.26(1, s), 7.99(1, s), 7.78(2, dd), 7.48(1, t), 6.88(1, bs), 6.54(1, s), 4.77(2, s), 3.82(3, s), 2.3–2.1(1, m), 2.1–1.9(1, m), 1.72(3, s), 0.97(3, t) |
| 7 | 8.27(1, s), 8.02(1, s), 7.86(1, d), 7.71(1, d), 7.47(1, t), 6.82(1, bs), 4.76(2, s), 4.42(2, dd), 3.81(3, s), 2.35–2.15(1, m), 2.1–1.9(1, m), 1.65(3, s), 0.90(3, t) |
| 8 | 8.12(1, s), 8.03(1, s), 7.77(2, dd), 7.47(1, t), 6.99(1, bs), 4.42(2, dd), 2.3–2.1(1, m), 2.1–1.9(1, m), 1.66(3, s), 1.39(9, s), 0.92(3, t) |
| 9 | 8.04(1, s), 7.83(1, s), 7.76(1, s), 7.70(1, s), 6.99(1, bs), 4.42(2, dd), 4.02(3, s), 2.35–2.2(1, m), 2.05–1.9(1, m), 1.64(3, s), 0.91(3, t) |
| 10 | 8.08(1, s), 7.84(2, d), 7.63(2, d), 6.84(1, bs), 4.41(2, dd), 4.02(3, s), 2.3–2.1(1, m), 2.0–1.8(1, m), 1.64(3, s), 0.89(3, t) |
| 11 | 8.06(1, s), 7.74(1, s), 7.57(1, s), 7.61(1, s), 6.81(1, bs), 6.53(1, s), 4.01(3, s), 2.3–2.0(2, m), 2.42(3, s), 1.69(3, s), 0.97(3, t) |
| 12 | 8.08(1, s), 7.77(1, s), 7.63(1, s), 7.58(1, s), 6.82(1, s), 4.43(2, dd), 4.02(3, s), 2.94(3, s), 2.35–2.15(1, m), 2.1–1.9(1, m), 1.64(3, s), 0.92(3, t) |
| 13 | 8.12(1, s), 8.01(1, s), 7.79(2, dd), 7.51(1, t), 6.73(1, bs), 4.29(2, dd), 4.03(3, s), 2.35–2.15(1, m), 2.05–1.85(1, m), 1.59(3, s), 0.96(3, t) |
| 14 | 8.47(1, s), 8.24(1, s), 7.71(1, d), 7.45(1, d), 6.97(1, bs), 4.41(2, dd), 4.04(3, s), 2.3–2.1(1, m), 2.05–1.8(1, m), 1.63(3, s), 0.90(3, t) |
| 15 | 8.08(2, s), 7.97(1, s), 7.69(2, s), 6.98(1, bs), |

TABLE 2-continued

| Example Number | 200 MHz, delta scale in ppm, Tetramethylsilane (TMS) standard, using $CDCl_3$ as solvent |
|---|---|
|  | 4.43(2, dd), 4.02(6, s), 2.3-2.1(1, m), 2.0-1.8(1, m), 1.62(3, s), 0.89(3, t) |
| 16 | 8.45(1, s), 8.29(1, s), 8.03-7.87(2, m), 4.62(2, dd), 4.02(3, s), 2.3-2.1(1, m), 2.0-1.8(1, m), 1.53(3, s), 0.92(3, t) |
| 17 | 8.10(1, s), 7.90(1, d), 7.80(1, d), 7.50(1, t), 7.30(1, s), 6.80(1, bs), 4.45(2, dd), 4.05(3, s), 2.30(3, s), 2.40-2.10(1, m), 2.10-1.80(1, m), 1.65(3, s), 0.90(3, t) |
| 18 | 8.65(1, s, exchange with $D_2O$), 8.15(1, s), 7.85(1, s), 7.65(1, s), 7.55(1, s), 7.50(1, s, exchange with $D_2O$), 4.45(2, s), 2.40(3, s), 2.05(2, m), 1.55(3, s), 0.90(3, t) |
| 19 | 7.75(4, bs), 6.91(1, bs), 4.45(2, dd), 4.05(3, s), 2.30(3, s), 2.40-2.10(1, m), 2.10-1.80(1, m), 1.65(3, s), 0.90(3, t) |
| 20 | 8.32(1, s), 7.73(2, s), 7.25(1, bs), 4.40(2, dd), 4.08(2, s), 3.95(1, s), 2.3-2.1(1, m), 2.0-1.8(1, m), 1.68(3, s), 0.89(3, t) |

EXAMPLE 21

The compounds of Examples 1-20 were tested in vitro for fungicidal activity and phytotoxicity.

A. The compounds were tested in vitro for fungicidal activity against *Pythium ultimum*, *Botrytis cinerea* and *Venturia inaequalis*.

Fungitoxicity assay against *Pythium ultimum*:

A dilution series of test compound was prepared in dimethylsulfoxide, and 0.1 milliliter (ml) of each dilution was added to 19.9 ml of a liquid asparagine-sucrose broth (YSB, Erwin, D. C. and Katznelson, K., 1971, Can. J. Microbiol. 7, 15) in 9 cm diameter petri dishes to give the desired concentrations of test compound. Each plate was inoculated with a mycelial plug, 7 millimeters (mm) in diameter, taken from the growing edge of a culture of *Pythium ultimum* grown on potato dextrose agar. Two replicate plates were used for each treatment. The increase in mycelial dry weight was determined after growth for 48 hours at 25° C. with shaking on a gyrotary shaker at 60 revolutions per minute (rpm). EC50 values were calculated from dose response curves. As used herein, the terminology "EC50" means the concentration of test compound required to inhibit growth by 50% as compared to a control lacking the test compound.

Fungitoxicity assay against *Botrytis cinerea*:

A dilution series of test compound was prepared in dimethylsulfoxide and 125 microliters (ul) of each dilution was added to 25 ml of molten potato dextrose agar to give the desired concentrations of test compound. The mixtures were poured immediately into 9 centimeter (cm) diameter petri dishes. Two replicate plates were used for each treatment. Each plate was inoculated with a 7 mm diameter plug taken from the growing edge of a 5 day old culture of *B. cinerea* on potato dextrose agar. Plates were incubated at 25° C. for 48 hours, then the colony diameters were measured and EC50 values calculated from dose response curves.

Fungitoxicity assay against *Venturia inaequalis*:

Test compounds were dissolved in dimethylsulfoxide at 1 milligram per milliliter (mg/ml), and 50 ul added to 950 ul of yeast extract-dextrose medium (YED, 0.4% yeast extract, 2% dextrose) to give 50 part per million (ppm) solutions. Minimum inhibitory concentration (MIC) values were determined using a microtiter assay with twofold serial dilutions of the prepared 50 ppm solutions (100 ul) in YED medium. Inoculum consisted of a spore suspension of *V. inaequalis* in YED medium at $2.5 \times 10^5$ spores per ml. Each well of the microtiter plates was inoculated with 100 ul of inoculum, and the plates incubated for 7 days at 25° C. before determination of MIC values.

Results of the testing for fungicidal activity against the above named fungi are set forth below in Table 3 as Pythium EC50 (ppm), Botrytis EC50 (ppm) and Venturia MIC (ppm), respectively.

B. The compounds were tested in vitro for phytotoxicity in a tobacco root elongation assay.

Tobacco root assay for Phytotoxicity:

A dilution series of test compound was prepared in dimethylsulfoxide and 20 ul of each dilution was added to 20 ml of molten nutrient medium, consisting of Murashige and Skoog salt base, 2% sucrose and 1% agar, to give the desired concentrations of test compound. The mixtures were poured immediately into 9 cm diameter petri dishes. Surface-sterilized tobacco seeds were placed on each plate (20 seeds per plate) and the plates incubated in a vertical position in a 27° C. incubator with a 16 hour photoperiod. After 7 days the mean root lengths were calculated, and EC50 values determined from dose response curves.

Results of the tobacco root assay are set forth below in Table 3 as Tob. EC50 (ppm).

TABLE 3

| Example | Pythium EC50 (ppm) | Tob. EC50 (ppm) | Botrytis EC50 (ppm) | Venturia MIC (ppm) |
|---|---|---|---|---|
| 1 | 0.31 | 1.86 | 9.50 | 1.56 |
| 2 | 1.61 | 4.94 | 71.30 | 12.50 |
| 3 | 2.07 | 5.35 | 21.80 | 6.25 |
| 4 | 68.40 | — | 68.90 | >25 |
| 5 | 16.30 | — | 54.60 | >25 |
| 6 | — | — | — | — |
| 7 | 22.81 | 9.48 | >100 | >25 |
| 8 | 172.60 | 46.80 | >100 | >25 |
| 9 | 0.05 | 0.06 | 0.25 | 0.05 |
| 10 | 1.57 | 21.70 | — | — |
| 11 | — | — | — | — |
| 12 | 0.16 | 0.38 | 0.28 | 0.10 |
| 13 | 7.38 | >20 | — | — |
| 14 | 4.68 | 1.25 | 28.10 | 25.00 |
| 15 | 4.16 | 2.33 | 4.19 | 1.56 |
| 16 | 0.58 | 11.31 | 12.60 | 6.25 |
| 17 | 24.20 | — | 97.30 | >25 |
| 18 | 5.95 | — | 53.90 | >25 |
| 19 | >10 | — | >100 | >25 |
| 20 | 0.23 | 1.00 | — | — |

EXAMPLE 22

The compounds of Examples 9 and 12 were tested in a microtiter plate assay for fungicidal activity against a variety of fungi over a range of different dosage rates.

The following organisms were employed in the test *Pythium ultimum* (PYU), *Phytophthora capsici* (PHY), *Piricularia oryzae* (PIR), *Botrytis cinerea* (BOC), *Fusarium roseum* (FUS), *Rhizoctonia solani* (RHI), *Cercospora beticola* (CER), *Colletotrichum lagenarium* (COL), *Monilinia fructicol* (MON), and *Pseudocercosporella herpotrichoides* (PSH).

All fungi were transferred and maintained on potato dextrose agar plates. To prepare inoculum, PYU and PHY were grown in asparagine-sucrose broth (ASB) in shake culture and FUS and RHI were grown in a yeast extract-dextrose broth (YDB). After 2 days growth the cultures were homogenized and diluted into fresh ASB (PYU and PHY) or YDB (FUS and RHI). Inoculum of PIR, BOC, COL, MON, CER and PSH were prepared by scraping conidia from the surface of cultures grown on PDA into YDB. The conidial suspensions were strained through a double layer of cheesecloth to remove any mycelial clumps. The various inoculum preparations were added in 175 ul aliquots to wells of 96-well microtiter plates with 2 replicate wells per treatment. Test compounds were dissolved in acetone/methanol (1:1) at a concentration of 10 mg/ml, then 5 ul of the solution is added to 245 ul of sterile water to give 200 ppm solutions. Aliquots (25 ul) of each solution were added to the inoculum in the microtiter plates to give a concentration of 25 ppm. Microtiter plates were incubated for 3 days at room temperature and fungal growth recorded as % control by comparison with control wells without test compound.

The results (expressed as percent inhibition of fungal growth) of the testing are presented in Table 4.

TABLE 4

| Example | BOC | CER | COL | MON | PHY | PIR | PSH | PYU | RHI | FUS |
|---|---|---|---|---|---|---|---|---|---|---|
| 9 | 90 | 100 | 90 | 100 | 100 | 100 | 100 | 100 | 90 | 75 |
| 12 | 100 | 100 | 100 | 100 | 100 | 100 | 100 | 100 | 0 | 0 |

EXAMPLE 23

A. Compound of Example 12 was tested for fungicidal activity against *Phytophthora infestans, Pseudoperonospora cubensis, Piricularia oryzae, Plasmopara viticola, Botrytis cinerea, Cercospora arachidicola* and *Venturia inaequalis* according to the procedures set forth below.

Tomato Late Blight (TLB)

Cultures of 1-2 week old *Phytophthora infestans* were maintained on V8 juice agar. Spore suspensions were used to inoculate tomato seedlings that were about two weeks old. A DeVilbiss atomizer was used to apply the spores to the fungicide treated foliage. The plants were kept in a humidity cabinet for 24 hours for infection and then placed in a controlled temperature chamber for disease development. Appropriate controls were included in each test for comparison purposes. Disease evaluations were made 6 days after inoculation and were recorded as "percent disease control", i.e., the relative efficacy of the test compound compared to no treatment, with 100% disease control indicating that the plants were observed to be disease free.

Tomato Late Blight—Curative (TLC)

The curative properties of the test compound were evaluated, using the same procedure as that set forth above in the section entitled "TOMATO LATE BLIGHT", except that the test compound was applied to the plants two days after inoculation with the pathogen.

Cucumber Downy Mildew (CDM)

Cultures of *Pseudoperonospora cubensis* were maintained on Bush Champion cucumbers. Spore suspensions were obtained by washing leaves to obtain the inoculum. A DeVilbiss atomizer was used to apply a suspension of spores to the lower leaves of the cucumbers. Following inoculation, the plants were kept in a humidity cabinet for 24 hours and then placed in a controlled temperature chamber. Disease evaluations were made seven days after inoculation and were recorded as percent disease control.

Downy Mildew of Grapes (GDM)

Cultures of *Plasmopara viticola* were maintained on grape seedlings derived from tissue culture. Leaves with sporulating mildew were rinsed in water to obtain the desired concentration of spores. A DeVilbiss atomizer was used to apply a suspension of spores to the lower leaves of the grape plants. The plants were kept in a humidity cabinet for 24 hours and then placed in a controlled temperature chamber for 7-8 days before scoring. Appropriate standards and control were included for comparison and disease evaluations were recorded as percent disease control.

Downy Mildew of Grapes—Curative (GDC)

The curative properties of the test compound were evaluated, using the same procedure as that set forth in DOWNY MILDEW OF GRAPES above except that the test compound was applied to the plants two days after inoculation with the pathogen.

Botrytis Gray Mold on Tomato (BOT)

Several strains of *Botrytis cinerea* were maintained on PDA for testing purposes. Spore suspensions of at least two strains were used to inoculate the plants. A dextrose solution was used to wash the spores from sporulating cultures. The combined spore suspension was applied with a DeVilbiss atomizer. Following inoculation the plants were placed in a controlled temperature chamber with 100% relative humidity for 5-7 days. Appropriate unsprayed controls and standards were used for comparison purpose and disease evaluations were recorded as percent disease control.

Peanut Cercospora (PC)

Inoculum of the early leaf spot pathogen *Cercospora arachidicola*, perfect stage *Mycosphaerella arachidis*, was cultured on PDA. Spores were obtained by washing the plates with water containing a surfactant at the rate of 1 drop per 100 ml. A concentration of 100,000 spores per milliliter was used to inoculate three week old peanut plants. Plants were inoculated and placed in a humidity cabinet at 100% relative humidity for 72 hours. The plants were then placed in a chamber with a 28° C. day temperature and a 24° C. night temperature. The chambers were set to provide intermittent misting to retain 90-95% relative humidity for the incubation period. Disease evaluations were made 16 days after inoculation and are reported as percent disease control.

Apple Scab (AS)

Locally collected isolates of *Venturia inaequalis* were cultured on PDA. Spore concentrations were obtained by washing the surface of sporulating plates. Two to three week old apple seedlings were inoculated with a spore suspension and placed in a controlled temperature chamber with intermittent mist and high relative humidity. Disease evaluations were made 14 days after inoculation and were recorded as percent disease control.

Rice Blast (RB)

*Piricularia oryzae* (about 20,000 conidia per ml) were used to inoculate Nato rice plants by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

Wheat Powdery Mildew (WPM)

*Erysiphe graminis* (f. sp. tritici) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

The fungicidal activity of compound of Example 12 against the above discussed phytopathogenic fungi is set forth in Table 5 as percent disease control at an application rate of 300 g/Ha.

TABLE 5

| Example | TLC | TLB | CDM | RB | BOT | PC | GDC | GDM | WPM |
|---|---|---|---|---|---|---|---|---|---|
| 12 | 99 | 100 | 99 | 75 | 100 | 80 | 50 | 100 | 75 |

EXAMPLE 24

The compounds of Examples 1 and 12 were tested in vivo for phytotoxic activity by applying the compounds to the foliage of cucumber, tomato, bean, lettuce and strawberry plants as a spray at a rate of 2200 g/Ha. The plants were evaluated seven days after spray application of the compounds.

Phototoxicity scores are set forth below in Table 6. The phytotoxicity scores use a symbol, "+", indicating presence of a plant growth regulatory effect as compared to a control to which a solvent mixture (acetone/water/methanol) lacking the test compound was applied. A zero indicates no apparent effect. Each score is a composite representing the mode value for three replicate plants.

TABLE 6

| Crop | Control | Example 1 | Example 12 |
|---|---|---|---|
| Cucumber | 0 | 0 | 0 |
| Tomato | 0 | 0 | 0 |
| Bean | 0 | 0 | 0 |
| Lettuce | 0 | 0 | 0 |
| Strawberry | 0 | + | 0 |

What is claimed is:

1. A compound of the formula:

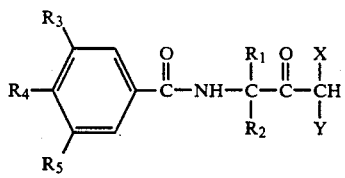

wherein:

$R_1$ and $R_2$ are each independently H, $(C_1-C_4)$alkyl, $(C_2-C_4)$alkenyl or $(C_2-C_6)$alkynyl;

$R_3$, $R_4$ and $R_5$ are each independently H, halo, $(C_1-C_4)$alkyl, $(C_2-C_6)$alkenyl, $(C_2-C_6)$alkynyl or $CR_6$=$NOR_7$, provided that at least one of $R_3$, $R_4$ and $R_5$ is $CR_6$=$NOR_7$;

$R_6$ is H, $(C_1-C_4)$alkyl, $(C_2-C_6)$alkenyl or $(C_2-C_6)$alkynyl;

$R_7$ is H, $(C_1-C_4)$alkyl, $(C_2-C_6)$alkenyl, $(C_2-C_6)$alkynyl or $(C_1-C_4)$alkylcarbonyloxy$(C_1-C_4)$alkyl; and X and Y are each independently H, halo, cyano, thiocyanato, isothiocyanato or $(C_1-C_4)$alkylsulfonyloxy; and agronomically acceptable salts thereof.

2. The compound of claim 1, wherein $R_1$ and $R_2$ are each $(C_1-C_4)$alkyl, $R_3$ is $CR_6$=$NOR_7$, $R_4$ is H, $(C_1-C_4)$alkyl or halo, $R_5$ is H, $(C_1-C_4)$alkyl, halo or $CR_6$=$NOR_7$, $R_6$ is H or $(C_1-C_4)$alkyl, $R_7$ is H, $(C_1-C_4)$alkyl or $(C_1-C_4)$alkylcarbonyloxy$(C_1-C_4)$alkyl, X is chloro or thiocyanato and Y is H or chloro.

3. The compound of claim 2, wherein Y is H.

4. The compound of claim 2, wherein $R_1$ ethyl, $R_2$ is methyl, $R_3$ is $CR_6$=$NOR_7$, $R_4$ and $R_5$ are each independently H, methyl or chloro, $R_6$ is H or methyl, $R_7$ is H, methyl or ethyl, X is chloro and Y is H or chloro.

5. The compound of claim 4, wherein Y is H.

6. The compound of claim 4, wherein $R_4$ is H and $R_5$ is chloro or methyl.

7. The compound of claim 4, wherein $R_6$ is H and $R_7$ is methyl.

8. The compound of claim 4, wherein $R_1$ is ethyl, $R_2$ is methyl, $R_3$ is $CR_6$=$NOR_7$, $R_4$ is H, $R_5$ is H, $CH_3$ or Cl, $R_6$ is H, $R_7$ is methyl, X is chloro and Y is H.

9. The compound of claim 2, wherein $R_1$ is ethyl, $R_2$ is methyl, $R_4$ is $CR_6$=$NOR_7$, $R_3$ and $R_5$ are each independently H or chloro, $R_6$ is H or methyl, $R_7$ is methyl, X is chloro and Y is H.

10. The compound of claim 2, wherein $R_1$ is ethyl, $R_2$ is methyl, $R_3$ and $R_5$ are each $CR_6$=$NOR_7$, $R_4$ is H, $R_6$ is H, $R_7$ is methyl, X is chloro and Y is H.

11. A fungicidal composition comprising an agronomically acceptable carrier and a fungicidally effective amount of the compound of claim 1.

12. A fungicidal composition comprising an agronomically acceptable carrier and a fungicidally effective amount of the compound of claim 2.

13. A fungicidal composition comprising an agronomically acceptable carrier and a fungicidally effective amount of the compound of claim 3.

14. A fungicidal composition comprising an agronomically acceptable carrier and a fungicidally effective amount of the compound of claim 4.

15. A fungicidal composition comprising an agronomically acceptable carrier and a fungicidally effective amount of the compound of claim 5.

16. A fungicidal composition comprising an agronomically acceptable carrier and a fungicidally effective amount of the compound of claim 6.

17. A fungicidal composition comprising an agronomically acceptable carrier and a fungicidally effective amount of the compound of claim 7.

18. A fungicidal composition comprising an agronomically acceptable carrier and a fungicidally effective amount of the compound of claim 8.

19. A fungicidal composition comprising an agronomically acceptable carrier and a fungicidally effective amount of the compound of claim 9.

20. A fungicidal composition comprising an agronomically acceptable carrier and a fungicidally effective amount of the compound of claim 10.

21. A method for controlling phytopathogenic fungi, comprising applying a fungicidally effective amount of the compound of claim 1 to plant foliage, plant seed or to a growth medium therefore.

22. A method for controlling phytopathogenic fungi, comprising applying a fungicidally effective amount of the compound of claim 2 to plant foliage, plant seed or to a growth medium therefore.

23. A method for controlling phytopathogenic fungi, comprising applying a fungicidally effective amount of the compound of claim 3 to plant foliage, plant seed or to a growth medium therefore.

24. A method for controlling phytopathogenic fungi, comprising applying a fungicidally effective amount of the compound of claim 4 to plant foliage, plant seed or to a growth medium therefore.

25. A method for controlling phytopathogenic fungi, comprising applying a fungicidally effective amount of the compound of claim 5 to plant foliage, plant seed or to a growth medium therefore.

26. A method for controlling phytopathogenic fungi, comprising applying a fungicidally effective amount of the compound of claim 6 to plant foliage, plant seed or to a growth medium therefore.

27. A method for controlling phytopathogenic fungi, comprising applying a fungicidally effective amount of the compound of claim 7 to plant foliage, plant seed or to a growth medium therefore.

28. A method for controlling phytopathogenic fungi, comprising applying a fungicidally effective amount of the compound of claim 8 to plant foliage, plant seed or to a growth medium therefore.

29. A method for controlling phytopathogenic fungi, comprising applying a fungicidally effective amount of the compound of claim 9 to plant foliage, plant seed or to a growth medium therefore.

30. A method for controlling phytopathogenic fungi, comprising applying a fungicidally effective amount of the compound of claim 10 to plant foliage, plant seed or to a growth medium therefore.

* * * * *